United States Patent [19]

Godfrey

[11] Patent Number: 5,420,349

[45] Date of Patent: May 30, 1995

[54] 2-AMINO-3-AROYL-BENZO[β]THIOPHENES AND METHODS FOR PREPARING AND USING SAME TO PRODUCE 6-HYDROXY-2-(4-HYDROXYPHENYL)-3-]BENZO[4-(2-AMINOETHOXY)-BENZOYL[β]THIOPHENES

[75] Inventor: Alexander G. Godfrey, Greenwood, Ind.

[73] Assignee: Eli Lilly and Company, Indianapolis, Ind.

[21] Appl. No.: 258,641

[22] Filed: Jun. 10, 1994

[51] Int. Cl.⁶ ............................................. C07C 327/44
[52] U.S. Cl. ......................................... 564/74; 558/230
[58] Field of Search ........................... 564/74; 558/230

[56] References Cited

U.S. PATENT DOCUMENTS

| | | | | |
|---|---|---|---|---|
| 4,133,814 | 1/1979 | Jones et al. | | 260/326.55 |
| 4,380,635 | 4/1983 | Peters | | 546/202 |
| 4,418,068 | 11/1983 | Jones | | 424/267 |

OTHER PUBLICATIONS

Geffken et al. *Chem Abstracts* 109:37500 (1988).
Ablenas et al., "Destabilized Carbocations", *Can. J. Chem.*, 65, 1800–1803 (1987).
Chippendale et al., "Condensed Thiophen Ring Systems", *J. C. S. Perkin I*, 1168–1172 (1974).
Reynaud et al., *Bul. Soc. Chem. Fr.*, 3623–3628 (1965).
Creary et al. "The Nature of Cationic Intermediates Derived From α-Thiocarbonyl Meglates", *J. Org. Chem.* 51, 7–15 (1986).
Schauman "Synthesis of Thioamides and Thiolactams", *Comp. Org. Syn*, vol. 6 419–434 (1990).
Cholod, "Cyanohydrins", Kirk-othmer *Encyclopedia of Chem Tech.*, vol. 7 3rd Ed. John Wiley & Sons, N.Y. 385–397 (1979).
Kobayashi et al., "A Facile Synthesis of Cyanohydrin Trimethylsilyl Ethers by the Addition Reaction of Trimethylsilyl cyanides with aldehydes under Basic Condition," *Chem. Lett.*, 537–540 (1991).
Tinapp, *Chem. Ber.*, 104, 2266–2272 (1971).

*Primary Examiner*—Peter O'Sullivan
*Attorney, Agent, or Firm*—James J. Sales; Gerald V. Dahling

[57] ABSTRACT

A group of 2-amino-3-aroyl-benzo[β]thiophenes are prepared by preparing an α-hydroxy thioacetamide by silyl mediated condensation of an aldehyde with an anion of dialkylamino thioformamide, cyclizing the α-hydroxy thioamide, and subsequently acylating the benzo[β]thiophene to yield the 2-amino-3-aryl derivative. These compounds may be treated with suitable phenyl Grignard reagents, and after deprotection, yield 6-hydroxy-2-(4-hydroxyphenyl)-3-[4-(2-piperidinoethoxy)benzoyl]benzo[β]thiophene.

6 Claims, No Drawings

2-AMINO-3-AROYL-BENZO[β]THIOPHENES AND METHODS FOR PREPARING AND USING SAME TO PRODUCE 6-HYDROXY-2-(4-HYDROXYPHENYL)-3-]BENZO[4-(2-AMINOETHOXY)-BENZOYL[β]THIOPHENES

BACKGROUND OF THE INVENTION

This invention relates to the field of pharmaceutical chemistry, and provides an advantageous process for preparing a group of 6-hydroxy-2-(4-hydroxyphenyl)-3-[4-(2-aminoethoxy)benzoyl]benzo[β]thiophenes. More specifically, the invention relates to methods for preparing 2-aminobenzo[β]thiophenes, novel 2-amino-3-aroyl-benzo[β]thiophenes, and the subsequent conversion of those thiophenes to the corresponding 2-(4-hydroxyphenyl) derivatives.

Kobayashi et al., *Chem. Lett.*, 537–540 (1991) teach the preparation of cyanohydrin trimethyl silyl ethers from aldehydes and trimethylsilyl cyamide (TMSCN). Creary and Mohammadi, *J. Org. Chem.*, 51: 7–15 (1986) describe the conversion of various cyanohydrins to the corresponding α-hydroxythioacetamides.

Ablenas et al., *Can. J. Chem.* 65: 1800–1803 (1987) teach the preparation of various 2-aryl-2-hydroxy thioacetamides and their subsequent cyclization to benzo[β]thiophenes with methane sulfonic acid (MeSO₃H).

Chippendale et al., *J. C. S. Perkin I*, 1168–1172 (1976) disclose the preparation of certain 2- and 3-(secondary amino)benzo[β]thiophenes.

Most of the compounds prepared by the process of this invention are taught in U.S. Pat. No. 4,133,814.

SUMMARY OF THE INVENTION

The present invention provides novel intermediates that allow for the convenient synthesis of 6-hydroxy-2-(4-hydroxyphenyl)-3-(4-hydroxybenzoyl)benzo[β]thiophenes having different functional groups on each of the three individual phenolic oxygens.

The invention also provides convenient methods for preparing α-hydroxythioacetamides in one reaction vessel without isolation of the intermediate products. These thioacetamides may subsequently be converted to 6-hydroxy-2-(4-hydroxyphenyl)-3-(4-hydroxyaroyl)-benzo[β]thiophenes having a variety of substituents on the phenolic oxygens.

Thus, the invention provides compounds of formula I:

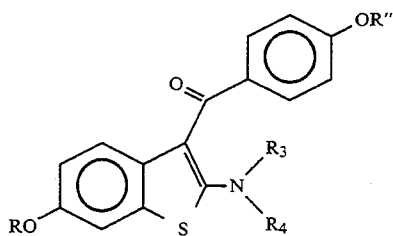

where R represents $C_1$-$C_6$ alkyl;
R″ represents $C_1$-$C_4$ alkyl or —$(CH_2)_nN(R_1)(R_2)$ where n is an integer of 1 to 4, and $R_1$ and $R_2$ are independently $C_1$-$C_4$ alkyl, or $R_1$ and $R_2$ combine to form $C_4$-$C_6$ polymethylene or —$(CH_2)_2O(CH_2)_2$—; and $R_3$ and $R_4$ are independently $C_1$-$C_6$ alkyl or combine to form $C_4$-$C_6$ polymethylene.

The invention also encompasses a process for preparing an α-hydroxythioacetamide of the formula:

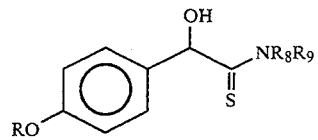

wherein R, $R_8$ and $R_9$ independently represent $C_1$-$C_6$ alkyl, which comprises:

(a) reacting an alkyl imidate of the formula:

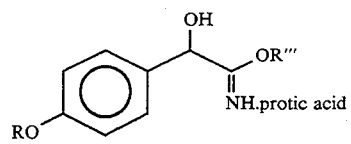

where R‴ is $C_1$-$C_6$ alkyl, with a sulfur compound to yield a thioester of the formula:

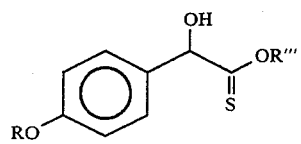

(b) reacting the thioester with a dialkylamine of the formula $NR_8R_9$ to yield the α-hydroxythioacetamide;

said reactions being conducted without isolation or purification of the thioester.

The invention also provides a convenient process for preparing 3-aroyl-2-phenylbenzo[β]thiophenes via 2-amino-3-aroyl-benzo[β]thiophenes. This process is especially well suited for the preparation of various 6-hydroxy-3-(4-hydroxybenzoyl)-2-(4-hydroxyphenyl)-benzo[β]thiophenes having differing groups on each phenolic oxygen. This process comprises:

(a) cyclizing the α-hydroxythioamide prepared above to form a 2-amino-benzo[β]thiophene;

(b) acylating the benzothiophene with an acylating agent of the formula:

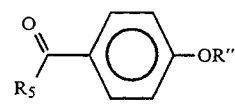

where R″ represents alkyl, aminoalkyl, or dialkylaminoethyl; to yield a 2-amino-3-aroyl-benzo[β]-thiophene; and (c) reacting the 2-amino-3-aroyl-benzo[β]thiophene with a phenyl Grignard reagent to yielding a benzo[β]thiophene of the formula:

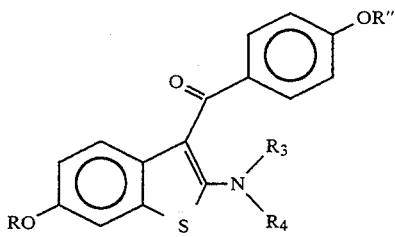

The invention further provides methods for preparing compounds of formula II:

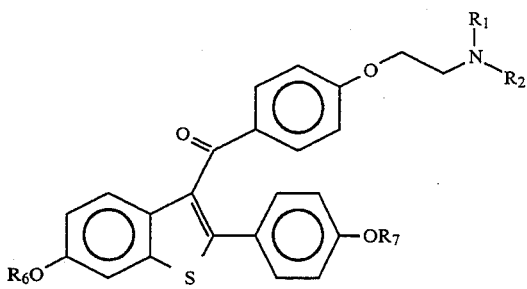

where $R_6$ and $R_7$ are hydrogen; comprising preparing a 3-aroyl-6-methoxy-(4-methoxyphenyl)benzo-[β]thiophene of formula I, where $R_6$ and $R_7$ are methyl, using the steps described above; and dealkylating the 3-aroyl-6-methoxy-(4-methoxyphenyl)-benzo[β]thiophene with a sulfur compound.

DETAILED DESCRIPTION OF THE INVENTION

In this document, all temperatures will be stated in degrees Celsius. All amounts, ratios, concentrations, proportions and the like will be stated in weight units, unless otherwise stated, except for ratios of solvents, which are in volume units.

In the formulas above the general terms bear their usual meanings. For example, the term $C_1$–$C_4$ primary or secondary alkyl refers to groups such as methyl, ethyl, propyl, s-butyl, i-butyl and the like. The term $C_1$–$C_4$ alkyl includes the above groups and also includes t-butyl. The term $C_1$–$C_4$ alkoxy refers to straight or branched chain lower alkoxy groups such as methoxy, ethoxy, propoxy, isopropoxy, butyloxy and the like. The term $C_4$–$C_6$ polymethylene refers to tetramethylene, pentamethylene and hexamethylene. The term $C_1$–$C_6$ alkyl includes the $C_1$–$C_4$ groups described above and various straight or branched chain pentyl and hexyl groups.

The term "substituted phenyl" refers to a phenyl molecule having one or two substituents selected from the group consisting of $C_1$–$C_4$ alkyl, $C_1$–$C_5$ alkoxy, hydroxy, nitro, chloro, fluoro, or tri(chloro or fluoro)methyl. "$C_1$–$C_5$ alkoxy" represents a $C_1$–$C_5$ alkyl group attached through a carbon bridge such as, for example, methoxy, ethoxy, n-propoxy, isopropoxy, and the like.

The following group of representative products of the process and of this invention will be mentioned, to assure that the reader fully understands the overall purpose of the process:

6-hydroxy-2-(4-hydroxyphenyl)-3-[4-(2-dimethylamino-ethoxy)benzoyl]benzo[β]thiophene;

3-[4-(2-ethoxymethylaminoethoxy)benzoyl]-6-hydroxy-2-(4-hydroxylphenyl)benzo[β]thiophene;

3-[4-(2-ethoxylisopropylaminoethoxy)benzoyl]-6-hydroxy-2-(4-hydroxyphenyl))benzo[β]thiophene;

3-(4-(2-dibutylaminoethoxy)benzoyl]-5-hydroxy-2-(4-hydroxyphenyl)benzo[β]thiophene;

3-[4-(2-(1-methylpropyl)methylaminoethoxy]-benzoyl]-6-hydroxy-2-(4-hydroxyphenyl)benzo[β]thiophene;

6-hydroxy-2-(4-hydroxyphenyl)-3-[4-[2-di(2-methylpropyl)aminoethoxy]benzoyl]benzo[β]thiophene;

6-hydroxy-2-(4-hydroxyphenyl)-3-[4-(2pyrrolidinoethoxy)benzoyl]benzo[β]thiophene;

6-hydroxy-2-(4-hydroxyphenyl)-3-[4-(2-piperidinoethoxy)benzoyl]benzo[β]thiophene;

6-hydroxy-2-(4-hydroxyphenyl)-3-[4-(2-morpholinoethoxy)benzoyl]benzo[β]thiophene;

3-[4-(2-hexamethyleneiminoethoxy)benzoyl]-6-hydroxy-2-(4-hydroxyphenyl)benzo[β]thiophene.

The final 6-hydroxy-2-(4-hydroxyphenyl)-3-[4-(2-aminoethoxy)benzoyl]benzo[β]thiophene compounds are tissue specific estrogenic agonist/antagonists and, thus, are useful for estrogenic, antiestrogenic and antiandrogenic therapy. Accordingly, they are useful in treating pathological conditions of endocrine target organs, which conditions are dependent or partially dependent on an estrogen or on an androgen. Such conditions include mammary cancer, mammary fibrocystic disease, cancer of the prostate, and benign prostatic hypertrophy.

U.S. Pat. No. 4,131,814 teaches that certain of the compounds are also useful as anti-cancer and anti-fertility drugs. The antiestrogenic and antiandrogenic efficacy of a preferred compound prepared by this invention, 6-hydroxy-2-(4-hydroxyphenyl)-3-[4 (2-piperidinoethoxy)benzoyl]benzo[β]thiophene, is explained in further detail in U.S. Pat. No. 4,413,068.

The dose of a compound to be administered to a human is rather widely variable. It should be noted that it may be necessary to adjust the dose of a compound when it is administered in the form of a salt, such as a laurate, the salt-forming moiety of which has an appreciable molecular weight. The general range of effective administration rates of the compounds is from about 0.05 mg/kg/day to about 50 mg/kg/day. A preferred rate range is from about 0.1 mg/kg/day to about 10 mg/kg/day, and the most highly preferred range is from about 0.1 mg/kg/day to about 5 mg/kg/day. Of course, it is often practical to administer the daily dose of a compound in portions at various hours of the day.

The route of administration of the compounds is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance.

The compounds are usually administered as pharmaceutical compositions. All of the usual types of compositions may be used including tablets, chewable tablets, capsules, solutions, parenteral solutions, troches, suppositories and suspensions. Compositions are formulated to contain a daily dose, or a convenient fraction of a daily dose, in a dosage unit, which may be a single tablet or capsule or a convenient volume of a liquid. In general, compositions contain from about 0.000006% to about 60% of compound, depending on the desired dose and the type of composition to be use.

The activity of the compounds does not depend on the composition in which it is administered or on the concentration of the composition. Thus, the compositions are chosen and formulated solely for convenience and economy.

The processes of the invention, leading to the 2-amino-3-aroylbenzo[β]thiophene intermediates and the the final compounds, 6-hydroxy-2-(4-hydroxyphenyl)-3-(4-hydroxybenzoyl)benzo[β]thio-phenes, are shown in Scheme I.

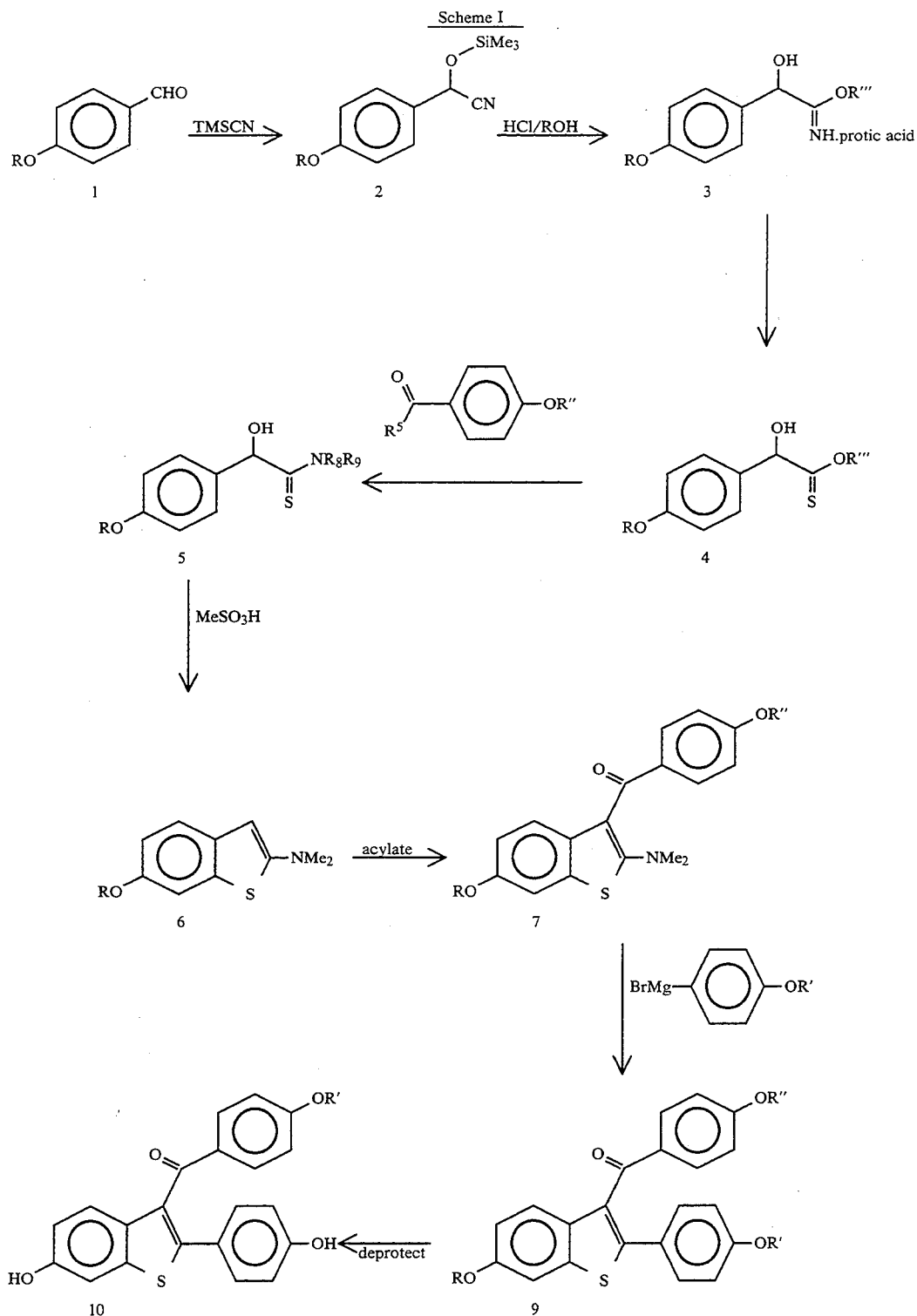

In Scheme I, R and R' independently represent $C_1$–$C_6$ alkyl, and R" represents a variety of alkyl or aminoalkyl groups. The various R, R', and R" groups which may be included in the compounds and methods of the invention will be evident in view of the following description of the process. In preferred embodiments, R" represents a 2-aminoethyl group, and more preferably, a 2-piperidinoethyl group. As is discussed more fully below, the 2-aminoethyl group may be present in the acylating agent during acylation or the acylating agent may contain a precursor of the 2-aminoethyl group.

2-AMINOBENZO[β]THIOPHENE FORMATION

The synthesis of the 2-aminobenzo[β]thiophene proceeds through the formation of a cyanohydrin which is converted to an alkyl imidate. Suitable temperatures for the formation of the cyanohydrin are from about 0° to about 100° C. The cyanohydrin forming reaction is tyically run for about 30 minutes to about 5 hours, i.e., until no more than an acceptable amount of either starting material remains. A preferred cyanohydrin is silylated cyanohydrin 2.

Alkyl imidate salt 3 is formed by treating the cyanohydrin with an alcohol in the presence of a protic acid. A preferred acid is hydrochloric acid while the preferred alcohol is ethyl alcohol forming the preferred imidate salt, an ethyl imino ether. Suitable temperatures for the formation of the imidate are from about −20° to about 60° C. The formation of the imidate salt is conducted with at least a small excess of alcohol and is typically complete after about 30 minutes to 6 hours. Longer reaction times may be required for slowly reacting cyanohydrins or at low temperatures. In preferred embodiments, the cyanohydrin may be converted directly to the imidate salt, and without isolation, directly to the thioamide. Of course, the imidate salt may optionally be isolated prior to conversion to the thioamide.

The conversion of the imidate salt to the thioamide is a "one-pot" reaction where the imidate is reacted with a sulfur compound to yield a thioester and the thioester is subsequently reacted with a suitable dialkylamine. This is essentially a direct conversion of the imidate to the thioamide without isolation or purification of the intermediate thioester. A preferred sulfur compound is hydrogen sulfide. Suitable solvents include pyridine and alcohols such as, for example, methanol, ethanol, or propanol. A preferred solvent for the conversion is ethanol. Any suitable amine, preferably a secondary amine, may be employed for the conversion; a preferred amine is dimethylamine.

According to the invention, two portions of dimethylamine are used. The first portion is approximately one equivalent of the amine and is used as a means of forming the free base of the imidate. The other, added after formation of the thioester with the sulfur compound, is employed as a nucleophile. The nucleophilic amine is added in an excess of from 1.1 to about 25, preferably from about 10-15, equivalents based on the amount of starting imidate. In a preferred embodiment, triethylamine is added to form the free amine from the imidate together with hydrogen sulfide to form the thioester, and then dimethylamine is added as a nucleophile yielding the thioamide.

In preferred embodiments, the imidate is initially stirred with the amine and sulfur compound at a temperature of from about −20° to 20° C. for from about 10 minutes to about 24 hours, and preferably at about 0° C. for approximately one hour. After stirring the imidate salt with the amine and H$_2$S gas, the second portion of amine is introduced and the reaction mixture stirred at a temperature of from about −20° to 20° C. for from about 10 minutes to about 24 hours, preferably at ambient temperature for about for 1-10 hours, and most preferably at ambient temperature for about 8 hours, to yield the α-hydroxythioacetamide.

After isolation, the α-hydroxythioacetamide is treated with a strong acid, such as, for example, methanesulfonic acid, in a solvent to effect ring closure forming the desired benzo[β]thiophene skeleton. Suitable solvents for the ring closure include methylene chloride. When the starting aldehyde is a p-alkoxy benzaldehyde such as anisaldehyde the sole product isolated is a 2-dialkylamino, 6-alkoxybenzo[β]thiophene. A particularly preferred 2-aminobenzothiophene results from anisaldehyde and is 6-methoxy-2-N,N-dimethylaminobenzo[β]thiophene.

The 2-dialkylaminobenzothiophene is then condensed with a suitable acid chloride to provide a 2-amino-3-aroylbenzo[β]thiopene in high yield after basic aqueous workup. A preferred solvent for the acylation is chlorobenzene.

ACYLATION

Acylation of the 2-aminobenzothiophene can be done with an acylating agent already containing the 2-aminoethyl (R″) group, yielding for example, the 2-piperidinoethoxy group of the desired product. Alternatively, acylation of the 2-aminobenzothiophene can be done with an acylating agent having a precursor of the 2-aminoethyl group. Such a precursor could be a group of the formula —(CH$_2$)$_n$X, where n is 0, 1 or 2 and X is a leaving group such as chlorine or bromine. The acylating agents are discussed in detail below.

It has been surprisingly discovered that acylation according to the invention may conveniently be carried out without using an acid scavenger such as carbonate or a tertiary amine. In fact, the addition of conventional tertiary amine acid scavengers can hinder or even terminate the reaction.

It has further been discovered that when (a) the R″ group of the acylating agent is —(CH$_2$)$_n$NR$_1$R$_2$, (b) the reaction is conducted in the presence of a protic acid such as hydrochloric acid, and (c) the R$_5$ group of the acylating agent is chloro, bromo or iodo, the acylation reaction is self-catalyzing. Without being bound by a particular theory, it is presently believed that the halogen generated during acylation regenerates the protic acid. Preferably, the acylation is conducted without the use of a traditional Friedel-Crafts catalyst. Since the reaction is self-catalyzing, no catalyst need be added. Nevertheless, a protic acid or an amino containing acylating agent complexed as a salt such as a hydrochloride salt may be added to effect acylation.

Accordingly, the acylation is essentially a modified Friedel-Crafts acylation, and may otherwise be carried out in the usual way. Optionally, either a Lewis acid or a proton acid may be used as a Friedel-Crafts catalyst; an excellent discussion of such catalysts appears in Olah, *Friedel-Crafts and Related Reactions, Interscience Publ.*, New York, London and Sidney, 1963, Vol. I, Ch. III and IV.

As explained by Olah, the classical Friedel-Crafts catalysts were Lewis acids. Such metal halides as aluminum chloride, aluminum bromide, and chloride, boron trifluoride, boron trichloride, boron tribromide, titanium tetrachloride, titanium tetrabromide, stannic chloride, stannic bromide, bismuth trichloride and ferric chloride are well known catalysts and are useful in this acylation.

The proton acid catalysts useful for this acylation include such substances as phosphoric acid, polyphosphoric acid, perchloric acid, chlorosulfonic acid, alkylsulfonic acids such as methanesulfonic and ethanesulfonic acids, toluenesulfonic and benzenesulfonic acids, sulfuric acid, chloroacetic acid and trifluoroacetic acid.

The acylation is ordinarily carried out in a solvent, and any inert organic solvent which is not significantly attacked by the conditions may be used. For example, halogenated solvents such as dichloromethane, 1,2-dichloromethane, chloroform and the like may be used, as can aromatics such as benzene, chlorobenzene and the like, alkanes such as petroleum ether, hexane and the like, and nitrohydrocarbons such as nitrobenzene and nitroalkanes.

Unlike traditional Friedel-Crafts acylation, acylation according to an embodiment of the invention can be carried out in the presence of toluene. Thus, it is not important to remove the toluene from materials prepared in earlier steps of the process.

The acylations may be carried out at temperatures from about the ambient temperature to about 100° preferably at the reflux temperature of the reaction mixture for processes catalyzed by the preferred proton acid catalyst, trifluoromethanesulfonic acid, and preferably at about ambient temperature for Lewis acid catalyzed processes.

The acylating agent is an active form of the appropriate benzoic acid, wherein $R_5$ is one of the recognized "active groups", such as chlorine atom, a bromine atom, or an activating ester. Appropriate activating esters are formed with hydroxybenzotriazole, acylimidazoles, nitrophenols, pentachlorophenol, N-hydroxysuccinimide, dicyclohexylcarbodiimide and the like. The group $R^5$ may also incidate an anhydride, especially a mixed anhydride such as those formed with small carboxylic acids such as acetic acid, formic acid and especially sulfonic acids.

The preferred acylating agents are these wherein $R_5$ is chloro or bromo. Thus, the most highly preferred individual acylating agents are 4-(2-piperidinoethoxy)-benzoyl chloride, 4-(2-pyrrolidinoethoxy)benzoyl bromide, 4-(2-pyrrolidinoethoxy)benzoyl chloride, 4-(2-pyrrolidinoethoxy)benzoyl bromide, 4-[2-(3-methylpyrrolidino)ethoxy]benzoyl chloride and 4-[2-(3-methylpyrrolidino)ethoxy]benzoyl bromide.

It is preferred to carry out the acylation steps in an inert halogenated solvent such as chloroform, dichloromethane, chlorobenzene, 1,2-dichloroethane and the like. In general, see as to such acylation reactions an article by Effenberger, *Angew. Chem. Int. Ed. Engl.* 19: 151–230 especially 163–165 (1980).

DISPLACEMENT

When the starting compound is acylated with an aroyl compound containing an aminoethoxy precursor, the amino group of the product is subsequently put in place by displacing the X group with the appropriate secondary amine. The X groups are leaving groups, preferably chloro or bromo, which are easily displaced by an amine according to known methods.

For example, the displacement is carried out in an inert solvent such as ketones in the nature of acetone or methyl ethyl ketone, esters such as ethyl acetate and propyl formate, alcohols such as methanol or ethanol, nitriles such as acetonitrile, or amides such as dimethylacetamide and dimethylformamide, or in such inert solvents as hexamethylphosphoramide, and in the presence of an acid scavenger such as alkali metal carbonates and bicarbonates and the like. At least an equimolar quality of acid scavenger is needed, and preferably a moderate excess. The displacement is carried out at ambient temperature, or may be carried out at moderately elevated temperatures from about ambient temperature to the reflux temperature of the reaction mixture.

More preferably, the displacement may be carried out in the additional presence of a catalytic amount of iodide ion, which acts as a catalyst for the displacement. When iodide is used in the mixture, the temperature range is lower, from about 0° to, preferably, the ambient temperature, although elevated temperatures are possible in some instances.

Further, the anion of the amine may be formed before the reaction is carried out, as by contact with a very strong base such as sodium hydride or an alkyl-lithium compound. The use of an anion does not otherwise change the manner in which the displacement is carried out, except that an acid scavenger is not needed.

MICHAEL ADDITION TO 2-AMINO, 3-AROYL-BENZOTHIOPHENE

Subsequent to acylation, the 2-amino, 3-aroylbenzothiophene is reacted with an appropriate Grignard reagent in a suitable solvent at a temperature of from about −78° C. to 20° C. In certain embodiments, the Grignard reagent may be reacted with the aminobenzothiophene in a refluxing solvent. Suitable solvents include ethyl ether and tetrahydrofuran. In a preferred embodiment, the Grignard reagent is generated from 4-bromoanisole and subsequently condensed with the 2-amino, 3-aroyl-benzothiophene in tetrahydrofuran at 0° C. to provide exclusively a 2-aryl-3-aroylbenzothiophene which comprises the basic carbon-framework of the desired final compounds. This reaction is a unique and unexpected 1,4-Michael addition of the Grignard reagent to the substrate with concomitant elimination of the dimethylamino group. This reaction surprisingly provides the 2-aryl-3-aroylbenzothiophene exclusively. In preferred embodiments, a stoichiometric amount of the Grignard reagent is employed to avoid product deterioration. None of the other possible products, i.e., compounds i–iv below, are observed.

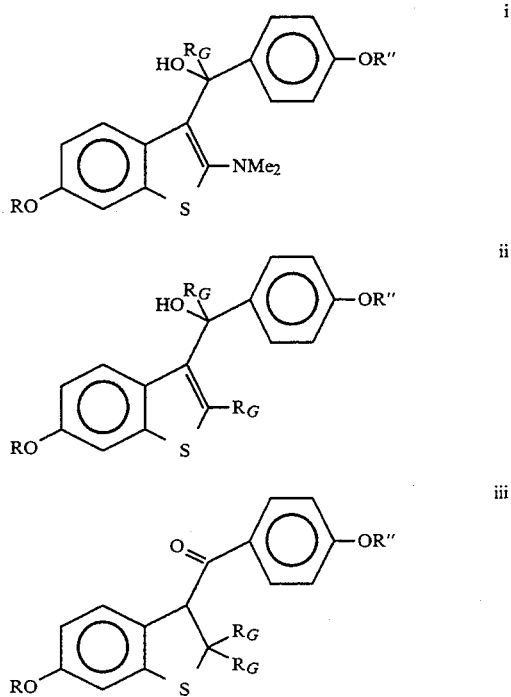

-continued

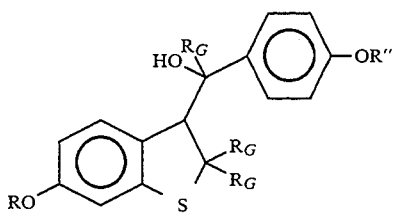

iv

DEPROTECTION OF 3-AROYL-ALKOXYBENZO[β]THIOPHENE

The dialkoxy benzo[β]thiophene may be deprotected to yield the desired dihydroxy final product by treating the 3-aroyl-dialkoxy material with a sulfur compound chosen from the group consisting of methionine and compounds of the formula

wherein X is hydrogen or unbranched $C_1$-$C_4$ alkyl, and Y is $C_1$-$C_4$ alkyl or phenyl.

The sulfur compounds are preferably, the alkylthiols, such as methanethiol, ethanethiol, the preferred agent, isopropanethiol, butanethiol and the like; dialkyl sulfides, such as diethyl sulfide, butyl s-butyl sulfide, ethyl propylsulfide, butyl isopropyl sulfide, dimethyl sulfide, methyl ethyl sulfide and the like; benzenethiol; methiomine, and alkyl phenyl sulfides such as methyl phenyl sulfide, ethyl phenyl sulfide, butyl phenyl sulfide and the like.

It has been found that the demethylation goes best when a substantial excess amount of the sulfur compound is used, in the range of from about 4 to about 10 moles per mole of the starting benzothiophene. The process can be carried out, although less efficiently, with a smaller amount of the sulfur compound in the range of about 2 or 3 moles per mole of starting compound, and to improve the yield by the addition of about 1 to 3 moles of an alkali metal halide, such as sodium, potassium or lithium chloride, iodide or or bromide. (A similar effect of sodium iodide is shown by Niwa et al., *Tet. Let.* 22: 4239-40 (1981)).

The demethylation reaction goes well at about ambient temperature, in the range of from about 15° to about 30°, and such operation is preferred. However, the demethylation step may be carried out at temperatures in the range of from about −30° to about 50° if it is desired to do so. Short reaction times in the range of about 1 hour have been found to be adequate.

In a preferred embodiment of the invention, the alkoxy protected 2-aryl-3-aroylbenzothiophene is diprotected by reacting the protected material with n-propanethiol and aluminum chloride in a halogenated solvent such as chlorobenzene.

After the product has been demethylated, it is recovered and isolated by conventional means. Simple variations in the isolation can provide the desired product as either the free amino compound or the hydrochloride salt of the amine.

All of the above reaction steps give acceptable yields when the stoichiometric amounts of the reactants are used, except as noted in certain specific steps above. As is normally the case in organic chemistry, improved yields are given by the use of an excess amount of one of the reactants, and it is practical to use an excess amount of the cheaper or the more easily obtained reactant. For example, in the formation of the protected starting compounds, it is practical and economical to use an excess of the acylating or sulfonating agent to assure complete reaction of the more expensive dihydroxy starting compound. Excesses in the range of from about 1% to about 25% are conveniently used, when an excess of one reactant is desired.

The compounds may form acid addition salts. The salts are conveniently formed, as is usual in organic chemistry, by reacting the compound prepared according to this invention with a suitable acid. The salts are quickly formed in high yields at moderate temperatures, and often are prepared by merely isolating the compound from a suitable acidic wash as the final step of the synthesis. For example, salts may be formed with inorganic or organic acids.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, α-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

All documents, e.g., patents and journal articles, cited above or below are hereby incorporated by reference in their entirety.

The invention is illustrated further by the following examples which are not to be construed as limiting the invention in scope or spirit to the specific procedures described in them. Many of the products were identified by nuclear magnetic resonance (NMR) analysis. Such analyses were run at 100 mHz in deuterochloroform unless stated otherwise.

EXAMPLE 1

Preparation of p-methoxybenzaldehyde cyanohydrin

Water (720 ml), sodium bisulfite (81 g, 0.775 mol, 1.2 equiv) and p-anisaldehyde (88 g, 0.646 mol, 1.0 equiv)

are combined, warmed to 40° C. and stirred for 3 hrs. The slurry is cooled to 5° C., and sodium cyanide (35 g, 0.711 mol, 1.1 equiv) in 140 ml water is added. The reaction is stirred for 2 hrs. at 5° C., then warmed to room temperature, and methyl-t-butyl ether (MTBE) (400 ml) added. The layers are separated after a brief stir, and the aqueous phase re-extracted with MTBE (100 ml). The combined organic layers were dried (MgSO$_4$), and concentrated to an oil, which was seeded to afford product: 69.5 g, 65.9%. The material can be recrystallized from toluene (3 ml per g substrate, heat to 35° C., cool to 5° C., 90% recovery).

EXAMPLE 2

Preparation of p-methoxybenzaldehyde cyanohydrin

To 49 g (1 mole) of sodium cyanide and 136 g (1 mole) anisaldehyde in ethyl alcohol 800 ml), containing triethylamine (5 mol %, 5.1 g) is added HCl gas (1 mol, 36.5 g) over 30 minutes at 5°–10° C. The resulting slurry is stirred at that temperature for 6 hours. In situ sampling of the reaction mixture shows the reaction to be complete. Additional HCl (0.2 moles) is added to quench the reaction. tHE solution is filtered and used in the next step without further purification. Yield, ca. 80%.

EXAMPLE 3

Preparation of Synthesis of p-methoxybenzaldehyde cyanohydrin iminoether hydrochloride (methyl imidate)

To the cyanohydrin prepared in Example 2, (1 mol, 153.2 g) in ethanol (ca. 800 ml) at room temperature is added HCl gas (73 g, 2 mol) over 30 min. The solution is warmed to 40°–50° C., and stirred for 6 hours. The solution precipitates product during the course of the reaction, and stirring is adjusted to ensure good mixing. At the completion of reaction, the product may be isolated by pulling vacuum on the solution carefully to remove HCl gas, then solvent exchanging into toluene at reduced pressure, with a temperature range to about 50° C. (Note). Alternately, and preferably, the slurry is taken directly into the next step. Yield, ca. 85–90%.

EXAMPLE 4

Preparation of α-(4-methoxy phenyl)-α-hydroxy-N,N dimethylthioacetamide

Hydrogen sulfide (0.427 g, 12.5 mmol, 1.5 equiv) was bubbled into a solution of the methyl imidate prepared in Example 3 (2.0 g, 8.6 mmol, 1.0 equiv) and triethylamine (0.958 g, 9.46 mmol, 1.1 equiv) in 20.0 ml of methanol at 0° C. After introduction of the gas, the reaction mixture was stirred for 1.0 hr. at 0° C. Next, gaseous dimethyl amine (4.2 g, 93.1 mmol, 11.2 equiv) was added and the resulting reaction mixture stirred at 0° C. for 1.5 hr. Product isolation involved concentration of the reaction mixture to ~⅓ the original volume. At this stage, the resulting precipitate is collected by filtration and dried to provide 1.3 g (70%) of N,N-dimethyl thioamide. mp. 101° C., TLC (100% ethyl ether, silica) R$_1$=00. $^1$HNMR (300 MHz, CDCl$_3$) d 7.32 (d, J=8.6 Hz, 2H), 6.83 (d, J=8, 1 Hz, 2H), 5.25 (s, 1H), 3.78 (s, 3H), 3.50 (s, 3H), 3.10(s, 3H).

EXAMPLE 5

Preparation of α-(4-methoxy phenyl)-α-hydroxy-N,N dimethylthioacetamide from p-methoxy benzoaldehyde cyanohydrin HCl (gaseous) is added to a solution of cyanohydrin prepared in Example 1 (9.96 g, 61.0 mmol, 1.1 equiv) in 50 ml of ethanol and allowing the resulting reaction mixture is stirred at room temperature overnight (~18 hrs). Next, at 0° C., triethylamine (15.25 g, 151 mmol, 2.47 equiv), followed by H$_2$S (3.72 g, 109.3 mmol, 1.8 equiv) was added to the reaction vessel. After 1 hr. of stirring at 0° C., dimethylamine (35 g, 776 mmol, 12.7 equiv) was introduced and the reaction mixture allowed to stir for ~8 hr. During that period the temperature rose from 0° C. to room temperature. The reaction mixture was concentrated to ~⅓ its volume. Based on $^1$HNMR, the reaction mixture was a 1:1 mixture of desired N,N-dimethyl thioamide and α-hydroxythioamide. Yield of desired product ca. 32%.

EXAMPLE 6

Preparation of 2-N,N-dimethylamino-6-methoxy benzo[β]thiophene

A sample of the α-hydroxythioamide prepared in Example 1 (40.0 g, 177 mmol) was dissolved in 1480 ml of methylene chloride. Methanesulfonic acid (57.0 ml, 888 mmol) was then added slowly with vigorous stirring (the reaction temperature was from 18.9° to 24.6° C.). The reaction was then allowed to proceed for 2 hours and (the reaction end point) was confirmed by TLC analysis, 40% ethyl acetate/hexanes, SiO$_2$). The reaction mixture (deep red solution) was then treated with 300 ml of aqueous saturated sodium carbonate followed by 100 ml of water with vigorous stirring. The layers were separated and the organic phase dried with solid sodium chloride (~5 g), decanted, and then concentrated under reduced pressure to yield a solid (51.0 g). This solid was then recrystallized from 200 ml of ethanol which yielded a yellow solid which was dried at 50° C. overnight under house vacuum. Obtained coarse yellow powder (29.2 g, 79%)

(Analytically pure sample has mp: 75°–76° C.) Analysis for C$_{11}$H$_{13}$NOS Calc.: C, 63.74; H, 6.32; N, 6.76 Found: C, 63.49; H, 6.32; N, 6.74

EXAMPLE 7

Preparation Of 2-N,N-dimethylamino-6-methoxy-3-[4-(d-piperidinoethoxy)benzoyl]benzo[β]thiophene A sample of the 2-dimethylaminobenzothiophene prepared in Example 2 (10.3 g, 49.8 mmol) and 4-(2-piperidinoethoxy)benzoyl chloride hydrochloride (15.9 g, 52.3 mmol) were partially dissolved in 100 ml of chlorobenzene. The mixture was warmed in a 100°–105° C. oil bath for 9 h. The mixture was then allowed to cool to room temperature over one hour. (Complete solidification of the mixture occurred on cooling).

The solidified mixture was then broken up and treated with aqueous saturated sodium carbonate (60 ml), followed by water (30 ml), then methylene chloride, then 50% aqueous sodium hydroxide (10 ml). After stirring for a short period, the mixture was diluted with 300 ml of methylene chloride and 100 ml of water. The layers were separated and the organic layer washed with 50% saturated sodium carbonate (40 ml). The layers were separated and the organic phase dried over solid sodium chloride (5 g), then decanted, and concentrated under reduced pressure to yield a thick dark oil (24.6 g). Purification was achieved by elution through an SiO$_2$ column (29×5 cm) with methylene chloride (1000 ml) followed by 5% methanol/methylene chloride (3000 ml). The fractions containing the desired product were collected and concentrated to yield a thick dark oil (19.8 g, 91% weight yield, 84% pure by H-NMR). Corr. yield=76%.

(Analytical purity could be achieved by recrystallization from acetonitrile, mp 209°-211° C. (decomp.)) Analysis for $C_{25}H_{30}N_2O_3S$ Calc.: C, 68.46; H, 6.89; N, 6.39; S, 7.31 Found: C, 68.19; H, 6.98; N, 6.32; S, 7.35

EXAMPLE 8

Preparation of 2-N,N-dimethylamio-6-methoxy-3-[4-(d-piperidinoethoxy)benzoyl]benzo[β]thiophene hydrochloride A sample of the 2-dimethylaminobenzothiophene prepared in Example 2 (104 mg, 0.50 mmol) and 4-(2-piperidinoethoxy)benzoyl chloride hydrochloride (152 mg, 0.50 mmol) were partially dissolved in 100 ml of toluene. The mixture was heated to reflux in a 120° C. oil bath for 16 h. The mixture was then allowed to cool to room temperature, and then filtered. The filter cake was allowed to air dry yielding a bright yellow powder (235 mg, 99% weight yield, 74% pure by HPLC). Corr. yield ca. 74%.

Analysis for $C_{25}H_{31cl}N_2O_3S$. Calc.: C, 63.21; H, 6.58; N, 5.90; S, 6.75; Cl, 7.46 Found: C, 63.09; H, 6.54; N, 5.76; S, 7.05; Cl, 7.61

EXAMPLE 9

Preparation of 2-(4-methoxyphenyl)-6-methoxy-3-[4-(piperidinoethoxy)benzoyl]benzo[β]thiophene hydrochloride A sample of the 3-aroyl,2-aminobenzothiophene prepared in Example 3, (252 mg, 0.575 mmol) was dissolved in 5 ml of THF in dry 25 ml of rbf equipped with a magnetic stir bar and septum under a dry nitrogen atmosphere. The solution mixture was chilled to 0° C. in an ice bath followed by the addition of a solution of 4-methoxyphenylmagnesium bromide (1.41 ml, 2.51 mmol, 1.78M in THF). After 10 minutes, the reaction mixture was treated with 10 ml of water then diluted with 20 ml of methylene chloride. The emulsion that forms was allowed to separate and the organic phase then separted, dried over $MgSO_4$, filter and concentrated to yield a yellow oil (384 mg). This crude mixture was then purified by silica column chromatography (methylene chloride-5% methanol/methylene chloride gradient). Obtained a light yellow oil (260 mg, 90% yield).

EXAMPLE 10

Preparation of 2-(4-methoxyphneyl)-6-methoxy-3-[4-(2-piperidinoethoxy)benzoyl]benzo[β]thiophene hydrochloride A sample of the 3-aroyl, 2-aminobenzothiophene (1.40 g, 3.19 mmol) prepared in Example 3 was dissolved in 15 ml of chlorobenzene in dry 50 ml rbf equipped with a magnetic stir bar and septum under a dry nitrogen atmosphere. The solution mixture was chilled to 0° C. in an ice bath followed by the addition of a solution of 4-methoxyphenylmagnesium bromide (2.4 ml, 4.27 mmol, 1.78M in THF). The reaction was allowed to proceed with slow warming to room temperature over 1 hour. The reaction mixture was then chilled to 0° C. and then treated with 30 ml of HCl saturated methanol. The dark mixture was then partially concentrated under reduced pressure to remove the methanol and excess HCl. A light colored soiild precipitates on standing and the mixture then filtered cold (0° C.) to yield a pale yellow soild (1.39 g, 88% weight yield, 85% pure by HPLC). Corr. yield=75%.

Material was correlated to authentic material via HPLC analysis.

EXAMPLE 11

Preparation of 6-hydroxy-2-(4-hydroxyphenyl)-3-[4-(2-piperidinoethoxy)benzoyl]benzo[β]thiophene hydrochloride A sample of the benzothiophene prepared in Example 6 (0.70 g, 1.3 mmol) was suspended in 10 ml of chlorobenzene. To this mixture was added aluminum trichloride (1.06 g, 8.0 mmol) in one part followed by addition of n-propanethiol (0.3 ml). The dark red mixture was then heated at 35° C. for 2.5 h. The reaction mixture was cooled in an ice bath (0° C.) followed by slow addition of 15 ml of THF. After 10 minutes of additional mixing, 10 ml of 6N aqueous HCl was added resulting in the formation of a precipitate. Stirring was continued overnight. The mixture was filtered and filter cake allowed to air dry overnight yielding 0.63 g of a yellowish white solid, 95% yield.

Material was correlated to authentic material via HPLC analysis.

From the foregoing it will be appreciated that, although specific embodiments of the invention have been described herein for purposes of illustration, various modifications may be made without deviating from the spirit and scope of the invention.

What is claimed is:

1. A process for preparing an α-hydroxythioacetamide of the formula:

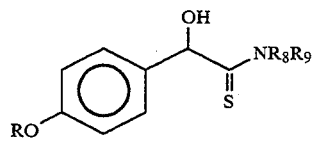

wherein R, $R_8$ and $R_9$ independently represent $C_1$–$C_6$ alkyl; comprising:
(a) reacting an alkyl imidate of the formula:

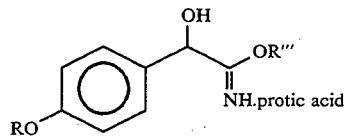

where R''' is $C_1$–$C_6$ alkyl, with a sulfur compound to yield a thioester of the formula:

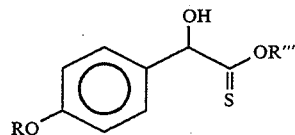

(b) reacting the thioester with a dialkylamine of the formula $HNR_8R_9$ to yield the α-hydroxythioacetamide;

said steps being conducted without isolation or purification of the thioester.

2. A process according to claim 1, wherein R is methyl.

3. A process according to claim 1, wherein $R_8$ and $R_9$ are methyl.

4. A process according to claim 1, wherein R''' is ethyl.

5. A process according to claim 1, wherein the protic acid is HCl.

6. A process according to claim 1, wherein the sulfur compound is ethanethiol.

* * * * *